US009381279B2

(12) United States Patent
Pacetti

(10) Patent No.: US 9,381,279 B2
(45) Date of Patent: Jul. 5, 2016

(54) IMPLANTABLE DEVICES FORMED ON NON-FOULING METHACRYLATE OR ACRYLATE POLYMERS

(75) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1308 days.

(21) Appl. No.: 12/763,113

(22) Filed: Apr. 19, 2010

(65) Prior Publication Data

US 2010/0266659 A1    Oct. 21, 2010

Related U.S. Application Data

(63) Continuation-in-part of application No. 11/089,774, filed on Mar. 24, 2005, now Pat. No. 7,700,659.

(51) Int. Cl.
| | |
|---|---|
| A61K 47/00 | (2006.01) |
| A61F 13/00 | (2006.01) |
| A61L 31/10 | (2006.01) |
| A61L 31/04 | (2006.01) |
| A61L 31/14 | (2006.01) |
| A61L 33/06 | (2006.01) |

(52) U.S. Cl.
CPC ............... *A61L 31/10* (2013.01); *A61L 31/048* (2013.01); *A61L 31/14* (2013.01); *A61L 33/064* (2013.01)

(58) Field of Classification Search
None
See application file for complete search history.

(56) References Cited

U.S. PATENT DOCUMENTS

| | | | |
|---|---|---|---|
| 4,000,958 A | 1/1977 | Hirooka et al. | |
| 4,117,235 A | 9/1978 | Taylor | |
| 4,156,034 A | 5/1979 | Mukoh et al. | |
| 4,273,760 A | 6/1981 | Koehler et al. | |
| 4,612,209 A | 9/1986 | Forgo et al. | |
| 4,931,287 A | 6/1990 | Bae et al. | |
| 4,954,424 A | 9/1990 | Mochiji | |
| 5,019,096 A | 5/1991 | Fox, Jr. et al. | |
| 5,163,952 A | 11/1992 | Froix | |
| 5,194,459 A | 3/1993 | Sato et al. | |
| 5,214,541 A | 5/1993 | Yamasita et al. | |
| 5,258,020 A | 11/1993 | Froix | |
| 5,314,770 A | 5/1994 | Yamasita et al. | |
| 5,334,468 A | 8/1994 | Yamasita et al. | |
| 5,357,636 A | 10/1994 | Dresdner, Jr. | |
| 5,385,795 A | 1/1995 | Yuasa et al. | |
| 5,422,207 A | 6/1995 | Yoda et al. | |
| 5,453,530 A * | 9/1995 | Byerley et al. | 558/252 |
| 5,500,760 A | 3/1996 | Varaprasad et al. | |
| 5,607,467 A | 3/1997 | Froix | |
| 5,616,338 A | 4/1997 | Fox, Jr. et al. | |
| 5,674,242 A | 10/1997 | Phan et al. | |
| 5,681,611 A | 10/1997 | Yoshikawa | |
| 5,684,913 A | 11/1997 | Sugiyama | |
| 5,721,299 A | 2/1998 | Angelopoulos | |
| 5,723,219 A | 3/1998 | Kolluri et al. | |
| 5,730,966 A | 3/1998 | Torgerson et al. | |
| 5,753,146 A | 5/1998 | Van Gemert et al. | |
| 5,770,115 A | 6/1998 | Misura | |
| 5,821,300 A | 10/1998 | Schneider | |
| 5,824,049 A | 10/1998 | Ragheb et al. | |
| 5,859,127 A | 1/1999 | Nakano et al. | |
| 5,873,904 A | 2/1999 | Ragheb et al. | |
| 5,879,713 A | 3/1999 | Roth et al. | |
| 5,910,854 A | 6/1999 | Varaprasad et al. | |
| 5,919,439 A | 7/1999 | Torgerson et al. | |
| 5,919,867 A | 7/1999 | Yasuda et al. | |
| 5,919,879 A | 7/1999 | Midha et al. | |
| 5,922,633 A | 7/1999 | Nakane et al. | |
| 5,929,173 A | 7/1999 | Midha et al. | |
| 5,932,299 A | 8/1999 | Katoot | |
| 5,962,138 A | 10/1999 | Kolluri et al. | |
| 5,980,878 A | 11/1999 | Torgerson | |
| 5,986,015 A | 11/1999 | Midha et al. | |
| 5,994,022 A | 11/1999 | Tanabe et al. | |
| 5,997,517 A | 12/1999 | Whitbourne | |
| 6,002,511 A | 12/1999 | Varaprasad et al. | |
| 6,039,872 A | 3/2000 | Wu et al. | |
| 6,083,393 A | 7/2000 | Wu et al. | |
| 6,096,070 A | 8/2000 | Ragheb et al. | |
| 6,099,563 A | 8/2000 | Zhong | |
| 6,110,483 A | 8/2000 | Whitbourne et al. | |

(Continued)

FOREIGN PATENT DOCUMENTS

| | | |
|---|---|---|
| EP | 0 243 160 | 10/1987 |
| EP | 1 192 959 | 4/2002 |

(Continued)

OTHER PUBLICATIONS

Wikipedia, (Hydroxyethyl)methacrylate, (accessed Jan. 10, 2010), pp. 1-2.*
Hamming, Lesely M., et al, Material Matters, (2008), 3.3, pp. 1-5.*
Vickers, N.J., et al, Grafting of PEG-Macromonomers to Plasma Polymers Using Ceric Ion Initiation, European Cells and Materials, (2005), vol. 10, Suppl. 2., p. 58.*
International Search Report for PCT/US2006/010420 filed Mar. 20, 2006, mailed Jan. 25, 2007, 14 pgs.
Tanaka et al., 21 Biomaterials 1471 Elsevier (2000).
Translation of Notice of Reasons for Rejection from JPO for Appl. No. P2008-503133, mailed Feb. 7, 2002, 2 pgs.

(Continued)

*Primary Examiner* — Brian-Yong Kwon
*Assistant Examiner* — Lyndsey Beckhardt
(74) *Attorney, Agent, or Firm* — Squire Patton Boggs (US) LLP

(57) ABSTRACT

Implantable devices formed of or coated with a material that includes a polymer having a non-fouling acrylate or methacrylate polymer are provided. The implantable device can be used for treating or preventing a disorder such as atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, or combinations thereof.

11 Claims, 1 Drawing Sheet

(56) References Cited

U.S. PATENT DOCUMENTS

| | | | |
|---|---|---|---|
| 6,113,883 A | 9/2000 | Midha et al. |
| 6,117,447 A | 9/2000 | Nakano et al. |
| 6,133,391 A | 10/2000 | Nielson et al. |
| 6,136,296 A | 10/2000 | Midha et al. |
| 6,143,354 A | 11/2000 | Koulik et al. |
| 6,154,306 A | 11/2000 | Varaprasad |
| 6,159,978 A | 12/2000 | Myers et al. |
| 6,165,455 A | 12/2000 | Torgerson et al. |
| 6,165,457 A | 12/2000 | Midha et al. |
| 6,174,329 B1 | 1/2001 | Callol et al. |
| 6,179,817 B1 | 1/2001 | Zhong |
| 6,180,632 B1 | 1/2001 | Myers et al. |
| 6,197,051 B1 | 3/2001 | Zhong |
| 6,197,844 B1 | 3/2001 | Hamrock et al. |
| 6,210,856 B1 | 4/2001 | Lin et al. |
| 6,214,901 B1 | 4/2001 | Chudzik et al. |
| 6,231,590 B1 | 5/2001 | Slaikeu et al. |
| 6,245,262 B1 | 6/2001 | Varaprasad et al. |
| 6,245,760 B1 | 6/2001 | He et al. |
| 6,246,508 B1 | 6/2001 | Yde-Andersen et al. |
| 6,248,129 B1 | 6/2001 | Froix |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,291,620 B1 | 9/2001 | Moad et al. |
| 6,299,604 B1 | 10/2001 | Ragheb et al. |
| 6,306,176 B1 | 10/2001 | Whitbourne |
| 6,344,035 B1 | 2/2002 | Chudzik et al. |
| 6,387,379 B1 | 5/2002 | Goldberg et al. |
| 6,420,036 B1 | 7/2002 | Varaprasad et al. |
| 6,423,787 B1 | 7/2002 | Kitano et al. |
| 6,440,429 B1 | 8/2002 | Torizuka et al. |
| 6,458,906 B1 | 10/2002 | Torgerson et al. |
| 6,482,834 B2 | 11/2002 | Spada et al. |
| 6,498,163 B1 | 12/2002 | Boschelli et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,532 B1 | 3/2003 | Torgerson et al. |
| 6,541,537 B1 | 4/2003 | Catena |
| 6,555,117 B2 | 4/2003 | Midha et al. |
| 6,592,990 B2 | 7/2003 | Schwantes |
| 6,627,584 B2 | 9/2003 | Ozbalik |
| 6,630,133 B1 | 10/2003 | Dupuis |
| 6,642,335 B2 | 11/2003 | Kawase et al. |
| 6,646,354 B2 | 11/2003 | Cobbley et al. |
| 6,663,855 B2 | 12/2003 | Frechet et al. |
| 6,685,925 B2 | 2/2004 | Frechet et al. |
| 6,727,344 B2 | 4/2004 | Weinert et al. |
| 6,746,770 B1 | 6/2004 | Afzali-Ardakani et al. |
| 6,939,376 B2 | 9/2005 | Shulze et al. |
| 7,005,137 B1 | 2/2006 | Hossainy et al. |
| 7,070,798 B1 | 7/2006 | Michal et al. |
| 7,083,646 B2 | 8/2006 | Valint, Jr. et al. |
| 7,094,256 B1 | 8/2006 | Shah et al. |
| 7,217,426 B1 | 5/2007 | Hossainy |
| 7,247,313 B2 | 7/2007 | Roorda et al. |
| 7,396,539 B1 | 7/2008 | Hossainy et al. |
| 7,563,454 B1 | 7/2009 | Pacetti |
| 7,699,886 B2 | 4/2010 | Sugimoto |
| 2001/0007083 A1 | 7/2001 | Roorda |
| 2001/0014717 A1 | 8/2001 | Hossainy et al. |
| 2001/0020011 A1 | 9/2001 | Mathiowitz et al. |
| 2001/0029351 A1 | 10/2001 | Falotico et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0064558 A1 | 5/2002 | Tanaka |
| 2002/0065551 A1 | 5/2002 | Koole et al. |
| 2002/0082679 A1 | 6/2002 | Sirhan et al. |
| 2002/0111590 A1 | 8/2002 | Davila et al. |
| 2002/0123801 A1 | 9/2002 | Pacetti et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083646 A1 | 5/2003 | Sirhan et al. |
| 2003/0083739 A1 | 5/2003 | Cafferata |
| 2004/0063805 A1 | 4/2004 | Pacetti et al. |
| 2004/0225345 A1 | 11/2004 | Fischell et al. |
| 2005/0106203 A1 | 5/2005 | Roorda et al. |
| 2006/0216326 A1* | 9/2006 | Pacetti .................... 424/426 |
| 2008/0015322 A1* | 1/2008 | Kindt-Larsen et al. ....... 526/320 |

FOREIGN PATENT DOCUMENTS

| | | |
|---|---|---|
| JP | 04 152952 | 5/1992 |
| JP | 2002-095756 | 5/1992 |
| JP | 11-089929 A | 4/1999 |
| JP | 2002-105136 | 4/2002 |
| JP | 2003-111836 | 4/2003 |
| JP | 2004-298223 | 10/2004 |
| JP | 2004-357826 | 12/2004 |
| WO | WO 00/02599 | 1/2000 |
| WO | WO 02/24249 | 3/2002 |
| WO | WO 2004/000383 | 12/2003 |
| WO | WO 2004/002546 | 1/2004 |

OTHER PUBLICATIONS

U.S. Appl. No. 10/376,348, filed Feb. 26, 2003, Ding et al.
"A more biocompatible oxygenerator New Terumo CAPIOX RX", Terumo Corp. Press Release 2000, www.terumo.co.jp/English/press/2000/00_03.html, downloaded Mar. 19, 2004, 2 pp.
"Biocompatible Coatings", Terumo Cardiovascular Systems, www.terumo-us.com/about_us/core_competencies/biocompatible_coatings.asp, downloaded Mar. 19, 2004, 1 p.
Braun, et al., "Polymer Synthesis: Theory and Practice", Fundamentals, Methods, Experiments, 3rd Ed., Springer, (book) 12 pp., 2001.
Chemical Book, 2-methoxyethyl methacrylate (accessed Dec. 3, 2015), pp. 1-2.
Handbook of Polymer Synthesis, Marcel Dekker Inc., Edited by H. R. Kricheldorf, 1992.
Imai, Biomaterials vol. 23, No. 1, pp. 44-45 (2005) without English translation.
Kenji Ikeda, Clinical Engineering vol. 9, No. 10, pp. 956-962 (1998) without English Translation.
Kocakulak et al., "Investigation of Blood Compatibility of PMEA Coated Extracorporeal Circuits", J. Bioactive and Compatible Polymers vol. 17, 2002, pp. 343-356.
Lim, VYT, et al, Singapore Med J, vol. 44(9) (2003), pp. 482-487.
Odian, Principles of Polymerization, 3rd ed. John Wiley & Sons, 18 pp., 1991.
Sigma-Aldrich, Ethyl tiglate (accessed Jul. 1, 2015) pp. 1-2.
Translation of Notice of Reasons for Rejection from Japanese Patent Office in application No. P2008-503133, mailed Feb. 7, 2002, 2 pp.
Translation of Notice of Reasons for Rejection from the Japanese Patent Office in application No. P2008-503133, mailed May 7, 2014 and its translation, 13 pp.

* cited by examiner

IMPLANTABLE DEVICES FORMED ON NON-FOULING METHACRYLATE OR ACRYLATE POLYMERS

CROSS-REFERENCE TO RELATED APPLICATION

This is a continuation-in-part application of U.S. application Ser. No. 11/089,774, filed on Mar. 24, 2005, the teaching of which is incorporated herein in its entirety by reference.

BACKGROUND OF THE INVENTION

1. Field of the Invention

This invention generally relates to coatings or implantable devices, such as stents or coatings on a stent, formed of a material that contains methacrylates or acrylates having non-fouling pendant groups.

2. Description of the Background

Although stents work well mechanically, the chronic issues of restenosis and, to a lesser extent, stent thrombosis remain. Pharmacological therapy in the form of a drug-delivery stent appears a feasible means to tackle these biologically derived issues. Polymeric coatings placed onto the stent serve to act both as the drug reservoir, and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

A current paradigm in biomaterials is the control of protein adsorption on the implant surface. Uncontrolled protein adsorption, leading to mixed layer of partially denatured proteins, is a hallmark of current biomaterials when implanted. Such a surface presents different cell binding sites from adsorbed plasma proteins such as fibrogen and immunoglobulin G. Platelets and inflammatory cells such as monocyte/macrophages and neutrophils adhere to these surfaces. Unfavorable events can be controlled by the use of non-fouling surfaces. These are materials, which absorb little or no protein, primarily due to their hydrophilic surface properties.

Another limitation of current drug-delivery stents stems from the fact that the stent is a foreign body. Use of drug-delivery stents has proved successful by use of controlled release of anti-proliferative or anti-inflammatory drugs to control restenosis. However, drug-delivery stents still have a small, but measurable, incidence of sub-acute thrombosis. Moreover, drug-delivery stents have not driven restenosis to zero levels, especially in more challenging patient subsets such as diabetics or patients with small vessels, and/or long, diffuse lesions. A biomaterials-based strategy for further improving the outcome of drug-delivery stents is by the use of biobeneficial materials or surfaces in stent coatings. A biobeneficial material is one which enhances the biocompatibility of a device by being non-fouling, hemocompatible, actively non-thrombogenic, or anti-inflammatory, all without depending on the release of a pharmaceutically active agent.

Some of the currently used polymeric materials such as poly(vinylidene fluoride-co-hexafluoropropene) have good mechanical properties, and acceptable biocompatibility, but also have low permeability to drugs. One proposed solution to ameliorate this issue is to blend in hydrophilic polymers. However, it is well known in the art that many hydrophilic materials such as polyethylene oxide or hyaluronic acid are water-soluble and can be leached out of the composition such that the coating may lose biobeneficiality. Such polymeric blends can also have compromised mechanical properties, particularly the ultimate elongation.

The present invention addresses such problems by providing a polymeric material for coating implantable devices by providing polymeric materials from which the device can be made.

SUMMARY OF THE INVENTION

Provided herein is a coating or implantable medical device formed of a polymer having non-fouling pendant groups.

In one embodiment, the polymer can be a polymer that contains repeating units of Formula I:

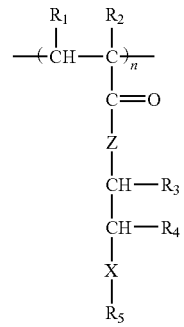

where:

$R_1$ and $R_2$ are independently H, $C_1$-$C_4$ alkyl, silyl groups, siloxy groups, or phenyl, $R_3$, and $R_4$, $R_5$ are independently H, $C_1$-$C_4$ alkyl, silyl groups, siloxy groups, phenyl, poly(ethylene glycol) (PEG), polypropylene glycol), or poly(alkylene oxide), Z is O, S or $NR_6$ where $R_6$ is H, $C_1$-$C_4$ alkyl such as $CH_3$, ethyl, propyl, isopropyl, isobutyl, sec-butyl, or n-butyl, or phenyl, X is absence, O, S, or $NR_7$ where $R_7$ is H, $C_1$-$C_4$ alkyl such as $CH_3$, ethyl, propyl, isopropyl, isobutyl, sec-butyl, or n-butyl, or phenyl, and n is a positive integer ranging from, e.g., 1 to 100,000.

In some embodiments, in the polymer of formula I, where Z is O, X can be absent, O, S, or $NR_7$ where $R_7$ is as defined above.

In some embodiments, in the polymer of formula I, where Z is S, X can be absent, O, S, or $NR_7$ where $R_7$ is as defined above.

In some embodiments, in the polymer of formula I, where Z is $NR_6$, X can be absent, O, S, or $NR_7$ where $R_6$ and $R_7$ are as defined above.

In some embodiments, in the polymer of formula I, where X is absent, Z is O, S or $NR_6$ where $R_6$ is as defined above.

In some embodiments, in the polymer of formula I, where X is O, Z is S or $NR_6$ where $R_6$ is as defined above.

In some embodiments, in the polymer of formula I, where X is S, Z is O, S or $NR_6$ where $R_6$ is as defined above.

In some embodiments, in the polymer of formula I, where X is $NR_7$, Z is O, S or $NR_6$ where $R_6$ and $R_7$ are as defined above.

In some embodiments, in the polymer of formula I, where Z is NH, X is NH.

In some embodiments, in the polymer of formula I, where Z is S, X is S.

In some embodiments, in the polymer of Formula I, X is O.

The polymer disclosed herein containing units of formula I can be a homopolymer or a copolymer. The copolymer can be statistical, random, alternating, period block or graft copolymer including the repeating units of Formula I and/or other repeating units such as a biocompatible polymer, and/or a biobeneficial material, both defined below.

The polymer defined herein can be used alone or in combination with another biocompatible polymer and/or a biobeneficial material to form coatings on implantable medical devices or to form the implantable medical devices themselves. In some embodiments, the coatings or medical devices optionally include a bioactive agent.

The polymer or polymer blends described herein can be used to form a coating(s) on an implantable device. The polymers or polymer blends described herein can also be used to form the implantable device itself. The implantable device can optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Figure 1:
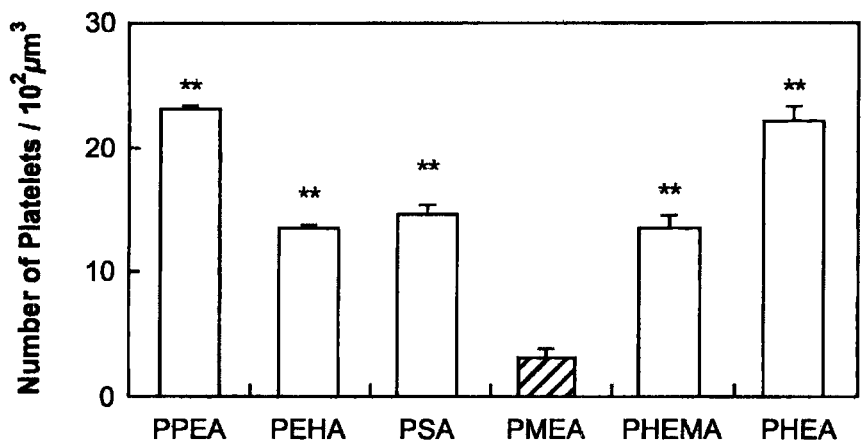
FIG. 1 shows the number of platelets adhered to the surface of a poly(methacrylate) polymer coating.

Provided herein is coating or implantable medical device formed of a polymer having non-fouling pendant groups. The polymer defined herein can be used alone or in combination with another biocompatible polymer and/or a biobeneficial material to form coatings on implantable medical devices or to form the implantable medical devices themselves. In some embodiments, the coatings or medical devices optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, ABT-578, clobetasol, prodrugs thereof, co-drugs thereof, and combinations thereof. The implantable device can be implanted in a patient to treat, prevent or ameliorate a disorder such as atherosclerosis, thrombosis, restenosis, hemorrhage, vascular dissection or perforation, vascular aneurysm, vulnerable plaque, plaque rupture in type 2 diabetes, chronic total occlusion, claudication, anastomotic proliferation for vein and artificial grafts, bile duct obstruction, ureter obstruction, tumor obstruction, or combinations thereof.

Polymers Formed of Monomers Having Non-Fouling Pendant Groups

In one embodiment, the polymer can be a polymer that contains repeating units of Formula I:

$$\mathrm{-\!\!\left(\!CH\!-\!\underset{\underset{\underset{\underset{\underset{R_5}{X}}{\underset{|}{CH\!-\!R_4}}}{\underset{|}{CH\!-\!R_3}}}{\underset{|}{Z}}}{\overset{R_1}{\underset{|}{C}}\!\!\overset{R_2}{\underset{|}{\underset{|}{C}}}}\!\right)_{\!\!n}\!\!-}$$

where:
$R_1$ and $R_2$ are independently H, $C_1$-$C_4$ alkyl, silyl groups, siloxy groups, or phenyl, $R_3$, and $R_4$, $R_5$ are independently H, $C_1$-$C_4$ alkyl, silyl groups, siloxy groups, phenyl, poly(ethylene glycol) (PEG), polypropylene glycol), or poly(alkylene oxide), Z is O, S or $NR_6$ where $R_6$ is H, $C_1$-$C_4$ alkyl such as $CH_3$, ethyl, propyl, isopropyl, isobutyl, sec-butyl, or n-butyl, or phenyl, X is absence, O, S, or $NR_7$ where $R_7$ is H, $C_1$-$C_4$ alkyl such as $CH_3$, ethyl, propyl, isopropyl, isobutyl, sec-butyl, or n-butyl, or phenyl, and n is a positive integer ranging from, e.g., 1 to 100,000.

In some embodiments, in the polymer of formula I, where Z is O, X can be absent, O, S, or $NR_7$ where $R_7$ is as defined above.

In some embodiments, in the polymer of formula I, where Z is S, X can be absent, O, S, or $NR_7$ where $R_7$ is as defined above.

In some embodiments, in the polymer of formula I, where Z is $NR_6$, X can be absent, O, S, or $NR_7$ where $R_6$ and $R_7$ are as defined above.

In some embodiments, in the polymer of formula I, where X is absent, Z is O, S or $NR_6$ where $R_6$ is as defined above.

In some embodiments, in the polymer of formula I, where X is O, Z is S or $NR_6$ where $R_6$ is as defined above.

In some embodiments, in the polymer of formula I, where X is S, Z is O, S or $NR_6$ where $R_6$ is as defined above.

In some embodiments, in the polymer of formula I, where X is $NR_7$, Z is O, S or $NR_6$ where $R_6$ and $R_7$ are as defined above.

In some embodiments, in the polymer of formula I, where Z is NH, X is NH.

In some embodiments, in the polymer of formula I, where Z is S, X is S.

In some embodiments, in the polymer of Formula I, X is O.

The polymer disclosed herein containing units of formula I can be a homopolymer or a copolymer. The copolymer can be statistical, random, alternating, period block or graft copolymer including the repeating units of Formula I and/or other repeating units such as a biocompatible polymer, and/or a biobeneficial material, both defined below.

Some representative polymers of Formula I are: poly(2-methoxyethyl acrylate) (PMEA), poly(2-hydroxyethyl acrylate) (PHEA), poly(ethyl acrylate) (PEA), (poly(2-ethylhexyl acrylate) (PEHA), poly(2-phenoxyethyl acrylate) (PPEA), poly(2-ethoxyethyl acrylate) (PEEA), poly(2-hydroxyethyl methacrylate) (PHEMA), poly(2-methoxyethyl methacrylate) (PMEMA), poly(ethyl methacrylate) (PEMA), (poly(2-ethylhexyl methacrylate) (PEHMA), poly(2-phenoxyethyl methacrylate) (PPEMA), poly(hydroxypropyl methacrylamide), poly(2-ethoxyethyl methacrylate) (PEEM), and combinations thereof.

In some embodiments, $R_1$, $R_2$, $R_3$, $R_4$, $R_5$, Z and X of Formula I are selected to exclude from Formula I any of the methacrylate or acrylate polymers described in the sections entitled "Polymer blends" or "Biobeneficial material", below.

The polymers described herein can be synthesized by methods known in the art (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992; G. Odian, Principles of Polymerization, $3^{rd}$ ed. John Wiley & Sons, 1991). For example, one method that can be used to make the polymer can be free radical methods (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992). Polymerization by suspension or emulsion techniques utilizing free radical initiation is commonly employed. Block copolymers and terpolymers can be produced by atom transfer polymerization. Polymerization in solvent can also be used to synthesize the polymers described herein.

Polymer Blends or Conjugation

In another embodiment, the polymers described herein can be blended with one or more additional biocompatible polymers having different hydrophilicity and/or flexibility to generate a polymer blend coating material that has desired biocompatibility, flexibility and drug permeability. In other embodiments, the polymers of the present invention can be bonded, conjugated, grafted or crosslinked with one or more additional biocompatible polymers. In some embodiments, the polymers can be coated in separate layers.

The additional biocompatible polymer can be biodegradable (both bioerodable or bioabsorbable) or nondegradable, and can be hydrophilic or hydrophobic. In some embodiments, hydrophilic is defined to have a Hildebrand solubility parameter δ value greater than about 8.5 $(cal/cm^3)^{1/2}$, e.g., greater than about 9.5 $(cal/cm^3)^{1/2}$, greater than about 10.5 $(cal/cm^3)^{1/2}$ or about 11.5 $(cal/cm^3)^{1/2}$. The δ is determined by the following equation:

$$\delta = (\Delta E/V)^{1/2}$$

where ΔE is the energy of vaporization, cal/mole, and V is the molar volume, $cm^3$/mole.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanoate), poly(4-hydroxyheptanoate), poly(4-hydroxyoctanoate) and copolymers including any of the 3-hydroxyalkanoate or 4-hydroxyalkanoate monomers or blends thereof, poly polyesters, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly (anhydrides), poly(tyrosine carbonates) and derivatives thereof, poly(tyrosine ester) and derivatives thereof, poly (imino carbonates), poly(glycolic acid-co-trimethylene carbonate), polyphosphoester, polyphosphoester urethane, poly (amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers other than the polymers of Formula I (defined above), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly (methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, alginate, fibrin, fibrinogen, albumin, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof. In some embodiments, the polymer can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), and poly(L-lactic acid-co-glycolic acid), respectively.

Biobeneficial Material

The polymers or polymer blends described herein may form a coating on an implantable device such as a stent or form the implantable device such as the stent optionally with a biobeneficial material. The combination can be mixed, blended, bonded, conjugated, crosslinked, grafted, or coated in separate layers. In some embodiments, it can be an interpenetrating polymer network (IPN). The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, albumin, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

The polymer of Formula I or a polymer blend or conjugation (e.g., bonded or grafted) having the polymer of Formula I may form a coating or an implantable device optionally with one or more bioactive agents. These bioactive agents can be any agent which can be a therapeutic, prophylactic, ameliorative or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic, prophylactic or ameliorative agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, and paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include midostaurin, pimecrolimus, imatinib mesylate, alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. In accordance with some other embodiments of the invention, bioabsorbable or non-degradable devices can be formed of a material containing the polymer of Formula I. The material can be the polymer of Formula I or a polymer blend containing the polymer of Formula I with one or more biocompatible polymers, optionally with a biobeneficial material and/or a bioactive agents, which are defined above. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Hemocompatibility Study of poly(2-methoxyethyl acrylate) (PMEA)

Figure 2:
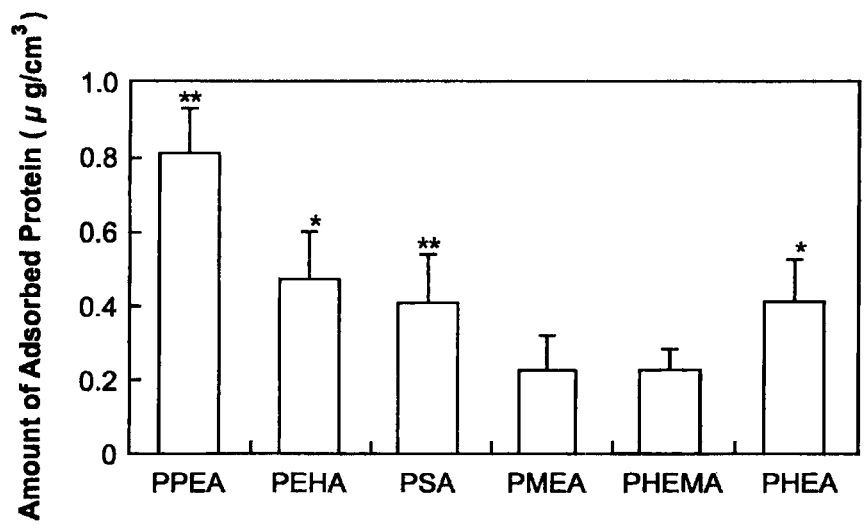
FIG. 2 shows the total amount of proteins from human plasma adsorbed onto the surface of a poly(methacrylate) polymer coating.

The measures of in vitro hemocompatibility, including human platelet adhesion, changes in platelet morphology, total absorbed protein from human plasma, amount of absorbed BSA (bovine serum albumin), absorbed human fibrinogen, and changes in protein conformation by circular dichroism of polymers PPEA, PEHA, PEA, PMEA, PHEMA and PHEA were measured (see M, Tanaka M, et al., Biomaterials 21:1471-1481 (2000)). FIG. 1 shows number of platelets adhered to the surface of the polymers (**$P<0.01$ vs. PMEA, mean±SD, n=5), and FIG. 2 shows the total amount of proteins from human plasma adsorbed onto polymers (*$P<0.05$ vs. PMEA; **$P<0.01$ vs. PMEA, mean±SD, n=5). In this statistical analysis, the P value comes from hypothesis testing to determine if, in fact, the levels of protein absorption between the various polymers are equivalent (null hypothesis). Here, P is the probability, on a scale of zero to one, of wrongly rejecting the null hypothesis if it is in fact true. Consequently, $P<0.05$ means there is less than a 5% chance that the difference seen between the two groups was caused by sampling error. This is often restated to mean there is a 95% confidence that the two groups are different.

As can be seen, the PMEA coating has both the lowest number of platelets absorbed and the lowest plasma protein absorption of the polymers tested.

Example 2

Fabrication of a Polymer-Coated Implantable Medical Device

Primer Layer

Poly(n-butyl methacrylate) is dissolved in 1:1 acetone: xylene (by weight) to give a 2% by weight solution. An EFD 780S spray nozzle with a VALVEMATE 7040 control system, manufactured by EFD, Inc., East Providence, R.I. is used to spray the polymer solution onto a stent. During the process of applying the composition, the stent can be optionally rotated about its longitudinal axis, at a speed of 50 to about 150 rpm. The stent can also be linearly moved along the same axis during the application.

The 2% solution of the polymer is applied to a 12-mm VISION™ stent (available from Guidant Corporation) in a series of 10-second passes, to deposit 10 μg of coating per spray pass. Between the spray passes, the stent is dried for 10 seconds using a flow of air at 80° C. Five spray passes are applied to form a 50 μg primer layer, followed by baking the primer layer at 80° C. for one hour.

Drug-Containing Layer

A mixture is prepared that consists of, by weight, 2% of poly(n-butyl methacrylate), 1.0% of everolimus, and 97% of the 1:1 (by weight) acetone:cyclohexanone. The same apparatus used to spray the primer layer on the stent is used to apply the drug layer. 10 spray passes are performed to form a 175 μg drug-polymer layer, followed by drying the drug-polymer layer at 50° C. for 1 hour.

Biobeneficial Topcoat Layer

A topcoat layer comprising, by weight, 2% poly(2-methoxyethyl acrylate) and 98% 60:40 acetone:cyclohexanone is then applied over the drug-containing layer using the same apparatus used to coat the primer layer and the drug-containing layer. Six spray passes are performed to form a 100 μg topcoat layer, followed by drying at 50° C. for 1 hour.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An stent having a coating comprising a polymer that comprises repeating units of Formula I:

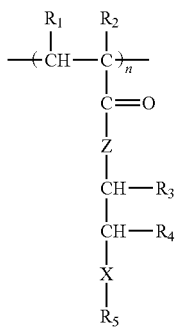

wherein:
$R_1$ and $R_2$ are independently H, C1-C4 alkyl, silyl groups, siloxy groups, or phenyl, $R_3$, $R_4$, and $R_5$ are independently H, C1-C4 alkyl, silyl groups, siloxy groups, phenyl, poly(ethylene glycol) (PEG), poly(propylene glycol), or poly(alkylene oxide), Z is S, X is absence, O, S, or $NR_7$ where $R_7$ is H, $CH_3$, ethyl, propyl, isopropyl, isobutyl, sec-butyl, n-butyl, or phenyl, and n is a positive integer ranging from 1 to 100,000.

2. The stent of claim 1,
wherein:
X is absent.

3. The stent of claim 1,
wherein:
X is O.

4. The stent of claim 1,
wherein:
X is S.

5. The stent of claim 1,
wherein:
X is $NR_7$.

6. The stent of claim 1,
wherein:
$R_3$, $R_4$, and $R_5$ are independently H, $CH_3$, ethyl, propyl, isopropyl, isobutyl, sec-butyl, n-butyl, or phenyl, silyl groups, siloxy groups, phenyl, poly(ethylene glycol) (PEG), poly(propylene glycol), or poly(alkylene oxide).

7. The stent of claim 1,
wherein:
$R_3$, and $R_4$ are independently H and $CH_3$; and
$R_5$ is silyl groups, siloxy groups, phenyl, poly(ethylene glycol) (PEG), poly(propylene glycol), or poly(alkylene oxide).

8. The stent of claim 1, further comprising a bioactive agent.

9. The stent of claim 8, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and a combination thereof.

10. A method of fabricating a stent, comprising forming on the stent a coating according to claim 1.

11. A method of treating a disorder in a patient comprising implanting in the patient the implantable device of claim 1, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

* * * * *